United States Patent
Hyde et al.

(10) Patent No.: US 8,674,694 B2
(45) Date of Patent: Mar. 18, 2014

(54) COIL SYSTEM AND METHOD FOR POST-EXPOSURE DOSIMETRY USING ELECTRON PARAMAGNETIC RESONANCE SPECTROSCOPY

(76) Inventors: James S. Hyde, Dousman, WI (US); Jason W. Sidabras, Milwaukee, WI (US); Richard R. Mett, Cedarburg, WI (US)

(*) Notice: Subject to any disclaimer, the term of this patent is extended or adjusted under 35 U.S.C. 154(b) by 368 days.

(21) Appl. No.: 12/868,244

(22) Filed: Aug. 25, 2010

(65) Prior Publication Data

US 2012/0112746 A1    May 10, 2012

Related U.S. Application Data (60) Provisional application No. 61/238,012, filed on Aug. 28, 2009.

(51) Int. Cl.
*H01J 49/00*    (2006.01)

(52) U.S. Cl.
USPC ........... 324/316; 324/300; 324/318; 600/411; 600/415; 433/29

(58) Field of Classification Search
USPC ......................................................... 324/316
See application file for complete search history.

(56) References Cited

U.S. PATENT DOCUMENTS

| | | | | |
|---|---|---|---|---|
| 2,656,842 A | * | 10/1953 | Ammarell | 132/73 |
| 4,725,779 A | * | 2/1988 | Hyde et al. | 324/318 |
| 4,866,387 A | * | 9/1989 | Hyde et al. | 324/318 |
| 5,680,047 A | * | 10/1997 | Srinivasan et al. | 324/318 |
| 6,054,856 A | * | 4/2000 | Garroway et al. | 324/318 |
| 7,084,628 B2 | * | 8/2006 | Swartz et al. | 324/316 |
| 2005/0057251 A1 | * | 3/2005 | Suits et al. | 324/318 |
| 2005/0146331 A1 | * | 7/2005 | Flexman et al. | 324/318 |
| 2006/0194198 A1 | * | 8/2006 | Licata | 435/5 |
| 2007/0247147 A1 | * | 10/2007 | Xiang et al. | 324/300 |
| 2011/0130647 A1 | * | 6/2011 | Swartz et al. | 600/421 |
| 2012/0040304 A1 | * | 2/2012 | Swartz et al. | 433/29 |

OTHER PUBLICATIONS

Reyes, R. A.; Electron Paramagnetic Resonance in Human Fingernails: the Sponge Model Implication; Jun. 27, 2008; Radiat Environ Biophys, 47; pp. 515-526.*

* cited by examiner

*Primary Examiner* — Melissa Koval
*Assistant Examiner* — Rishi Patel
(74) *Attorney, Agent, or Firm* — Boyle Fredrickson, S.C.

(57) ABSTRACT

An apparatus and method for triaging patients according to radiation exposure operates by measuring electron paramagnetic resonance spectra of fingernails, toenails, and/or teeth. A coil structure allows in vivo measurement of tooth enamel or fingernail keratin with reduced coupling to underlying tissue.

11 Claims, 6 Drawing Sheets

FIG. 13 ced

In an international climate where perpetual enemies, India and Pakistan, are both nuclear powers, where North Korea has nuclear weapons and Iran—a country that has threatened Israel, a country widely believed to be a nuclear power—may soon acquire them, the risk of a nuclear attack or terrorism is increasingly significant. Further, with recent high oil prices and a worldwide resurgence of nuclear power to produce electricity without emitting greenhouse gasses, there is a significant risk of nuclear accident. Nuclear accidents have also resulted from improper disposal of radioactive materials, such as radiation treatment machines.

In nuclear attack, nuclear improper-disposal events, and nuclear accident, there may be people potentially exposed to ionizing radiation while not carrying previously-issued dosimeters. Both nuclear attack and nuclear accident could be mass-casualty situations with several hundred to tens of thousands of people potentially exposed to radiation.

The Chernobyl, Goiánia, Hiroshima, and Nagasaki events each involved at least some deaths from acute radiation syndrome, as have other events. These events also generated demands for measurements of radiation exposure in many thousands of individuals of widely varying radiation exposure, resulting in a substantial stress on the medical systems.

In mass casualty situations there is often mass hysteria, where large numbers of 'worried-well' people physically unaffected by the event may believe that their lives are in danger and may even exhibit psychosomatic symptoms of exposure. This phenomenon is expected to occur in nuclear events such as nuclear attack, terrorism, or accident. Further, there are likely to be limited medical facilities available after some such events—treatment of everyone, the 'worried well' as well as the exposed, is not expected to be possible immediately after a major event.

It is desirable to be able to rapidly sort large numbers of people into categories which may include: those who are 'worried well;' those with minimal exposure—possibly sufficient to cause increased cancer rates or otherwise need follow up—but who will not need treatment for acute radiation sickness; those who have received significant exposure but should recover from acute radiation sickness with conventional therapy; those who should recover from acute radiation sickness with aggressive therapy such as marrow transplants; and those who will probably die regardless of treatment. In the short term, treatment can then be focused upon those groups who most likely will benefit from the treatment. The process of sorting people according to radiation dose or other injuries into treatable, urgently treatable, or untreatable groups is known as triage, and was formalized for non-radiological injuries by the French army as a way to handle the large number of casualties generated on World War I battlefields. Further, if radiation dose can be approximately quantified, this information can be used to help guide patient transport and treatment by determining which people will likely survive with simple supportive care, which will need advanced care such as transfusions, and which will need more drastic measures such as bone-marrow transplant to survive.

In the event of nuclear attack, communications are likely to be disrupted over a large area. In particular, centralized databases, remote locations, the internet, and the cell and landline telephone networks are likely to be nonfunctional or unreachable.

Existing technologies for determining which people of a population have been exposed to large doses of radiation include a differential blood count; neutrophils decrease in number because of bone marrow suppression and lack of replacement, while lymphocytes may undergo apoptosis. Unfortunately, not only do such counts require repeated measurements made by skilled medical staff, but baseline counts are unlikely to be available for the majority of people needing screening and both neutrophil and lymphocyte counts may undergo drastic changes from other causes ranging from HIV infection and stress to infection. A better method of triaging the potentially radiation exposed is needed.

Within a testing machine, the sample is measured by EPR resonance spectrometry in a magnetic field of at least two thousand gauss, and preferably about three thousand three hundred gauss—a field strength where resonance should occur at about nine to 9.5 gigahertz. The resonance is determined in an embodiment by sweeping frequency of a radio frequency source and observing absorption of radio frequency energy by, and ringing at the end of pulses of radio frequency energy caused by, presence of the sample. In an alternative embodiment, the resonance is determined by sweeping the magnetic field while providing repeated pulses of radio frequency energy and observing absorption of radio frequency energy by, and ringing at the end of pulses of radio frequency energy caused by, presence of the sample.

In an embodiment, an EPR reference standard such as a manganese dioxide resonance reference sample or a molybdenum compound reference sample is present within the magnetic field while the resonance is being measured. This reference sample provides an additional marker resonance at a frequency or magnetic field different from that of the RIS and MIS signals expected from radiation-exposed fingernail, but at a frequency close enough to provide a calibration reference usable as a reference for both magnetic field intensity or frequency position and intensity of the resonances.

In large-scale disasters, subject's recalled history alone has proven to not always be a good indicator of exposure to toxic or radioactive materials and corresponding need for treatment. Similarly, apparent physical injuries and symptoms are not good indicators of intensity of radiation doses received by a subject. When a radiation disaster, whether by accident like Chernobyl, or weapon like Hiroshima, happens, medical care systems will likely be overloaded. To best use available resources, the triage information is used to quickly sort (or triage) potential victims into categories of:

a. those who are unexposed or exposed below the detection threshold of the system.
b. those who have received detectable doses of radiation, but these doses are small enough that they will probably recover without need for treatment for acute radiation sickness;
c. those who have received significant doses requiring conventional, conservative, treatment, for radiation sickness; which may include transfusions of blood products, prophylactic antibiotics, nursing care, and nutritional support;
d. those who can possibly be saved by aggressive treatment such as bone marrow transplant; and
e. those who will die despite any reasonably available treatment, and to whom hospice therapy may be offered.

Typically, emergency workers are trained to tie a color-coded triage tag to each victim assessed during a large-scale disaster. Typically, green is used to indicate those who will survive without immediate treatment—these may wait many hours for evacuation or further assessment or may be sent home depending on circumstances, yellow for those who need some near-term care but are not in critical condition—these may wait for transportation or treatment but not as long as those coded green, red for those who require immediate treatment to survive and who receive priority transportation or treatment, and black for those who are expected to not survive even if given the best available treatment. Preprinted triage tags with perforated tear-strips for removing colored regions are often provided for use in such situations. Each tag has red, green, yellow, and black-colored regions and white space for other information; when attached to a victim the colored regions distant to the colored region of color appropriate to that victim are removed by emergency medical personnel by tearing along the perforations. Other systems of tags may provide color-coded stickers for attaching to tags. Victim identity, assessment of injuries, and other information may be written in the white spaces. Once patients are tagged, they are evacuated and/or treated in order of priority.

SUMMARY

A device for positioning resonators during EPR of fingernails in vivo has sensor loops in a partial glove for holding the resonators adjacent to fingertips. An alternative device for positioning sensor loops during EPR of fingernails has elastomeric cups for several fingertips that position resonators on the dorsal surface of the fingers adjacent to the fingernails. An alternative device for positioning resonators during EPR of fingernails has hollows for the fingers with coils placed adjacent to the dorsal surface of the fingertips. An alternate device for positioning resonators during EPR of toenails may use analogous devices to any of the above configured for the foot. All four devices combine with a permanent magnet for providing the magnetic field required for resonance, radio frequency apparatus, and a signal processing system to measure a radiation induced EPR signal from fingernails.

A device for EPR of teeth in vivo has sensor loops in a plastic chip that can be held between the teeth. The devices for EPR of teeth and fingernails are used to determine EPR spectra that provide a measure of radiation exposure of a subject, a measure which may be of use in triage following a release of radioactive materials or a nuclear attack.

DETAILED DESCRIPTION OF THE EMBODIMENTS

Figure 1:
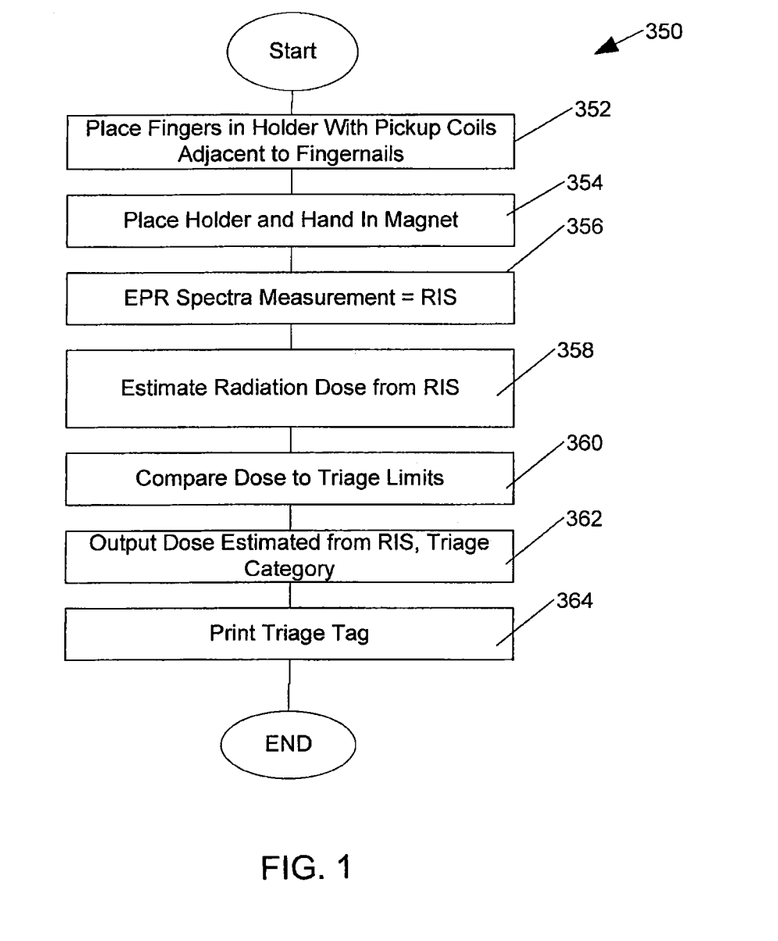
FIG. 1 is a flowchart of a rapid triage method wherein radiation exposure is detected by in-vivo measurements of EPR spectra in fingernails.

Radiation-induced EPR spectrum components (RIS) in fingernails and toenails may also be detected in vivo, according to the method 350 of FIG. 1. This eliminates generation of the MIS signals intrinsic to the process of clipping, and may provide more accurate results. Further, this permits excluding residual MIS signals from fingernail edges cut during pre-exposure normal grooming by placing the coils on a more proximal portion of the fingernail. In this method 350, a subject's hand is placed 352 in a holder such that pickup coils are retained adjacent to the dorsal surface of the fingers adjacent to the fingernails. The pickup coils are preferably positioned sufficiently proximal to the ends of the fingers that no mechanically-induced signal from recent clipping of the fingernails will be detected, yet sufficiently distal that the coils are adjacent to fingernail and not skin. The pickup coil has the property that its electromagnetic field interacts primarily with the fingernail and not the nailbed, thereby making it feasible to use high frequency EPR in vivo. The subject's hand is then placed 354 between the poles of a magnet. A RF measurement and processing system then measures 356 the radiation-induced EPR signal (RIS) from the fingernails, and uses a precomputed calibration curve to estimate 358 an estimated whole-body radiation dose of the subject based on the RIS EPR signal and assuming even irradiation of the subject. Should the subject lack or have injuries to her hands, or should limb-differential radiation dose information be desired, the subject's toenails are used in place of, or in addition to, the fingernails.

The estimated radiation dose is compared 360 to triage limits, and radiological triage information is output 362 by a display system to a system operator. A radiological triage tag may also be printed 364. Some events likely to cause large numbers of radiological injuries, such as nuclear attack, are also likely to cause non-radiological injuries such as burns, fractures, abrasions, and lacerations. The radiological triage information is then used, together with assessment of non-radiological injuries the subject may have sustained, to assist triage personnel in determining whether and what kind of treatment is offered to the subject.

Figure 2:
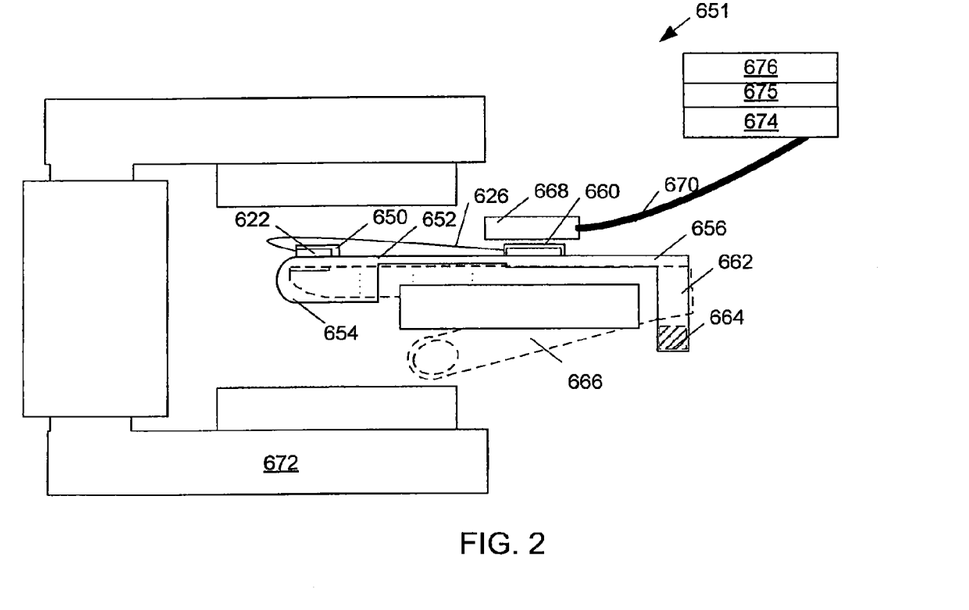
FIG. 2 is a schematic diagram of a device for holding coupling coils adjacent to the fingernails for EPR measurements.

A particular embodiment of a holder for retaining pickup coils in position on the dorsal surface of a subject's fingers is illustrated with apparatus 651 for measuring the EPR resonances of the fingernails in FIG. 2.

This alternative embodiment has a resonator 620 (FIG. 6) having from two to five plastic chips 622 cast from a flexible plastic and containing pickup coils 624 that will conform to the curvature of the top of a subject's fingernails. In an embodiment, a small sample of an EPR standard material 623 may also be embedded in the plastic chip 622. The pickup coils 624 in the plastic chips 602 are coupled by transmission line portions 626 and 628 to a coupling coil 630. In an embodiment, transmission line portions 626 are coaxial cable portions, in an alternative embodiment, transmission line portions 626 are twisted-pair portions, and the pickup coils 624, transmission line portions 626, and coupling coil 630 are formed from a single, larger, insulated, twisted wire loop.

Figure 6:
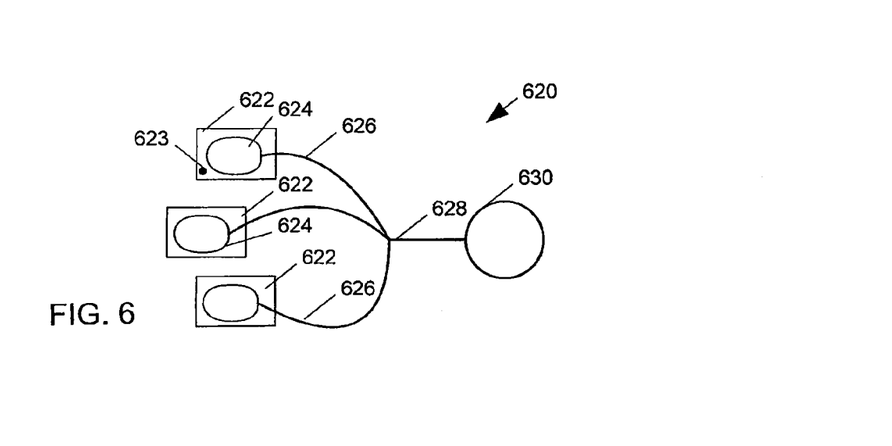
FIG. 6 is a top view of a sensing loop device suitable for sensing EPR spectra in enamel of the teeth and/or keratin of the fingernails.

The plastic chips 622 of the resonator of FIG. 6, with pickup coils 624, typically comprising one or two turns of copper wire, are inserted into pockets 650 (FIG. 2) in the dorsal surface of finger cups 654 of a thin elastomeric partial glove 652 having two to five finger cups 654 attached by elastomeric straps to a backhand portion 656 positionable above the back of the subject's hand. The glove 652 holds the plastic chips 622 near, and above, the subject's fingernails when the subject's fingertips are inserted into the finger cups 654 such that the pickup coils 624 are adjacent the dorsal surface of each fingertip and the pickup coils 624 are adjacent the subject's fingernails. In an embodiment, the elastomeric partial glove is made as a single piece from silicone rubber. The pickup coils 624 are connected by transmission sections 626, 628, to a coupling coil 630 that is inserted into a pocket 660 of the backhand portion 656. A wrist strap 662 having a hook and loop fastener 664 serves to secure the partial glove 652 to a subject's hand 666.

The hand, wearing the partial glove 652, is then inserted between poles of the magnet 672 and coupling coil 610 is held close to a second coupling coil 668 that is in turn connected by a coaxial transmission line 670 to apparatus 674 for measuring a radio-frequency EPR spectrum. As with the other embodiments herein described, the resonances measured are fed to a processing system 675 for determining an estimated radiation dose from the spectrum, and a printer 676 for printing a triage tag or sticker, The second coupling coil 668 is magnetically coupled to the coupling coil 610 of the resonator and permits the apparatus 674 for measuring a radio-frequency resonance to measure EPR resonances of the fingernails. The EPR spectrum is measured and an approximate whole-body radiation dose is calculated therefrom according to the method of FIG. 1 or as otherwise described herein.

The coupler having pickup coils 624 of from one to two turns of copper wire in the plastic chips 622, coupled by twisted-pair transmission line portions 626 and with a coupling coil 630 operates in a magnetic field of about 400 gauss with resonances at approximately 1.2 gigahertz. This embodiment may also operate at some higher frequencies.

The device of FIG. 2 has advantage in that it is self-adjusting for many different lengths and diameters of a subject's fingers, and widths of the subject's fingers, hands and wrists because the silicone rubber elastomeric material stretches to accommodate fingers of various sizes.

Figure 3:
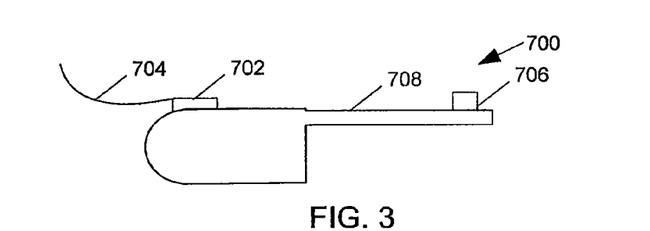
FIG. 3 illustrates a device having finger-cups for holding coupling coils adjacent to the fingernails for EPR measurements

In an alternative embodiment, three finger-cups 700 as illustrated in FIG. 3 are used, one for each of the index, second, and ring fingers of a subject's hand. Each finger cup 700 has a pickup coil 702 in position such that it will center over a subject's fingernail when a finger is inserted into the finger cup 700, the coil 702 is attached by a flexible cord 704 to RF measurement electronics. The finger-cup 700 also has apparatus, such as a button 706 or screw-hole in an elastomeric strap 708 for securing it to a machine. Elastomeric strap 708 permits self-adjustment for some variations in finger lengths.

Figure 4:
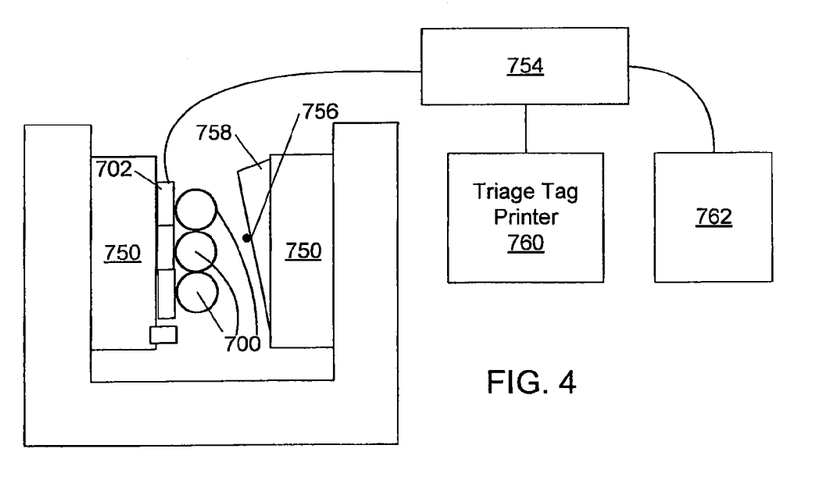
FIG. 4 is a schematic diagram of a machine for performing EPR measurements from fingernails.

The three finger cups 700 are attached to and suspended between poles 750 of a magnet (FIG. 4) with pickup coils 702 connected to the RF measurement and computing electronics 754. A reference 756 containing a standard such as manganese dioxide or a molybdenum compound is also present between the poles 750. A subject is invited to place an appropriate number of her fingertips, bearing fingernails, into the finger-cups 700 and the machine is activated to perform EPR on all three (or in an alternative embodiment, four) fingernails simultaneously. In an alternative embodiment, an optional plate 758 is present to create a gradient in the magnetic field between poles 750 to permit separate measurement of the three fingernails; the separate measurements may be combined into a total dose for the subject or may be reported separately. Once measurements are determined, a radiological triage tag or triage tag sticker may be printed on printer 760 and a patient record in a database on a recordkeeping database computer 762 may be updated with the measurements and triage category determined by the measurement and computing device 754.

Whole-body radiation dose measurements may also be made by measurements of EPR resonances in the enamel of human teeth, such as molars.

Prior techniques of measuring EPR resonances in human teeth have required either tooth removal, or use of a semirigid waveguide for coupling the apparatus for measuring radio frequency resonances to the teeth in vivo. It is not practical to remove teeth for screening large numbers of potential victims during or after a mass disaster—as such removal is likely permanent and tooth removal will likely be resisted by the potential victims. While the use of a semirigid waveguide as known in the art is feasible, the use of the EPR spectrometry in the field, as necessary for triage applications, is greatly simplified by use of a flexible connector or transmission line attached to a flexible pickup coil. Resolution of lower doses of radiation is made easier by combining information derived from measurements from more than one tooth and/or more than one fingernail.

Figure 5:
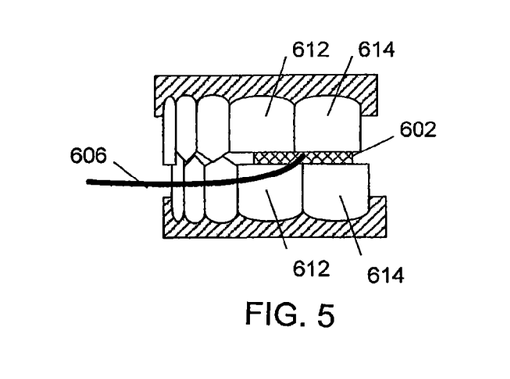
FIG. 5 is a side view of a sensing loop device clenched between teeth of a subject.
Figure 8:
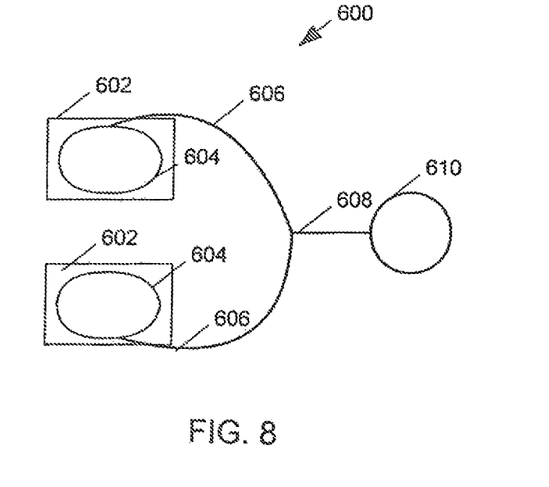
FIG. 8 is an illustration of a sensing loop device for use between teeth of a subject.

The embodiment of FIGS. 5 and 8 utilizes a resonator comprising a thin plastic chip 602 of thickness between one and two millimeters, of width six millimeters, and of length about one centimeter. This replaceable resonator greatly resembles the resonator previously described with reference to FIG. 6, but the plastic chips 602 and sensing coils 604 are somewhat larger and sturdier than those used with fingernails. Each such plastic chip 602 has embedded within it a sensing coil 604 of one to two turns of enameled copper wire and average diameter of seven millimeters. Each of the two sensing coils 604 is coupled through a twisted transmission section 606 to a common transmission section 608 and to a pickup coil 610 of about one centimeter diameter. The pickup coil 610 may either be a continuous loop, or may have a capacitive pigtail tuning element. The capacitive pigtail tuning element represents a point where the pickup coil loop is discontinuous; with its two ends twisted tightly together for a distance that provides suitable coupling capacitance between the ends.

In use, the plastic chips are clenched between a subject's upper and lower first molars 612 and second molars 614, thereby providing coupling to enamel of these teeth, four on each side and eight total, for EPR sensing. Other teeth also may be used, depending on the dental health of the subject, but this requires use of separate calibration data tables. The pickup coil is magnetically coupled by appropriate wire to apparatus for measuring a radiofrequency resonance as with the embodiment of FIG. 2. The assembly of chips, transmission sections, and pickup coil is essentially as for the device of FIG. 6, although larger diameter wire may be used; a wire loop is formed, transmission sections are pinched together and twisted, and remaining sections form sensing and pickup loops. The sensing coils, and optionally the coupling coil, are then cast into the plastic chips, and the entire assembly coated with insulating plastic. The simple construction of the plastic chips and associated transmission sections and pickup coils allows for low cost and easy replacement, as these components are likely to suffer eventual damage when chewed by large numbers of people. In an embodiment, the chips are made for one time use, eliminating need for sterilization of chips or replacement of chip covers between uses.

In use, the device of FIG. 8 is placed into the subject's mouth and clenched between teeth. The subject's head is then inserted between poles of a magnet wide enough to allow placement of the head between pole pieces, and EPR spectra are measured. In an embodiment, the magnet is preferably about 400 gauss and the resonance occurs at about twelve hundred megahertz when measuring EPR of teeth and using a coupler having pickup coils 604 of from one to two turns of copper wire embedded in the plastic chips 602, coupled by twisted-pair transmission line portions 606 to a coupling coil 610. Since teeth are relatively dry and absorption of radio frequency energy by water is not as significant an issue as with intact, uncut, fingernails, this embodiment also is expected to operate at 2.4 GHz with an appropriate magnetic field, and may also operate at some higher frequencies—possibly even at 9.5 GHz. In those subjects where radiation exposure is detected, a nonuniform magnetic field may be used to separately determine resonances from left and right teeth to detect asymmetrical exposure or invalid data due to improper chip placement, tooth loss or decay, or dental work on one or more teeth. Where valid data is obtained from both left and right teeth this data may be averaged to provide a more accurate measure of subject radiation exposure.

This use is illustrated with the use of molar teeth, but it also can be used with any teeth, so that in subjects with missing molars or extensively restored molars, the measurements may still be made using premolars, canines, and incisors, although different calibration tables may need to be used because of the reduced mass of enamel near the coils 604. For example, in subjects lacking molars, the plastic chips of the device of FIGS. 8 and 5 may be held between lip and upper incisors to obtain dosimetry information from the enamel of the incisors.

The device of FIG. 8 provides a measure of total radiation exposure of the subject since the teeth formed, which may often include some radiation exposure incurred by the subject many years before the measurement is made. The cumulative radiation dose includes radiation received from most causes such as the normal environment at 3 to 4 mSv per year and diagnostic X-rays at from 0.1 mSv for a chest X-ray to 10 mSv for a CT-scan, is typically well below the one Sievert or higher level that requires triaging into the medical system for treatment of acute radiation sickness. Therapeutic radiation to the oral cavity or neck may also have resulted in a prior exposure to teeth that would appear to be in the range of requiring acute medical treatment if received as a whole body exposure, this eventuality could be uncovered with appropriate medical history taking and by estimation of dose with EPR of fingernails in those subjects.

There is little biological difference between fingernails and toenails. Both have high keratin content and will develop both mechanically induced signals when clipped, although growth rate and average thickness may differ. Both will develop radiation induced EPR signals when exposed to ionizing radiation. They have some differences in detail, such as moisture content and thickness, because toenails generally grow at a slower rate. The machines described herein with respect to fingernail dosimetry are applicable to toenail dosimetry as well, although it may prove necessary to use separate stored calibration information for toenails and fingernails in measurement and computing apparatus FIG. 4, 754.

Measurement of radiation exposure using EPR fingernails of both hands and toenails of both feet may also prove useful to guide treatment in those subjects who have received radiation doses substantial enough to require treatment because differences in RIS between limbs can indicate when subjects have received uneven exposure. This is important because those subjects who have received uneven exposure may have more viable bone marrow or stem cells in those limbs that have received lower exposure than in those body parts that received higher exposure, and the viable bone marrow or stem cells may seed those body parts that received higher exposure.

Figure 7:
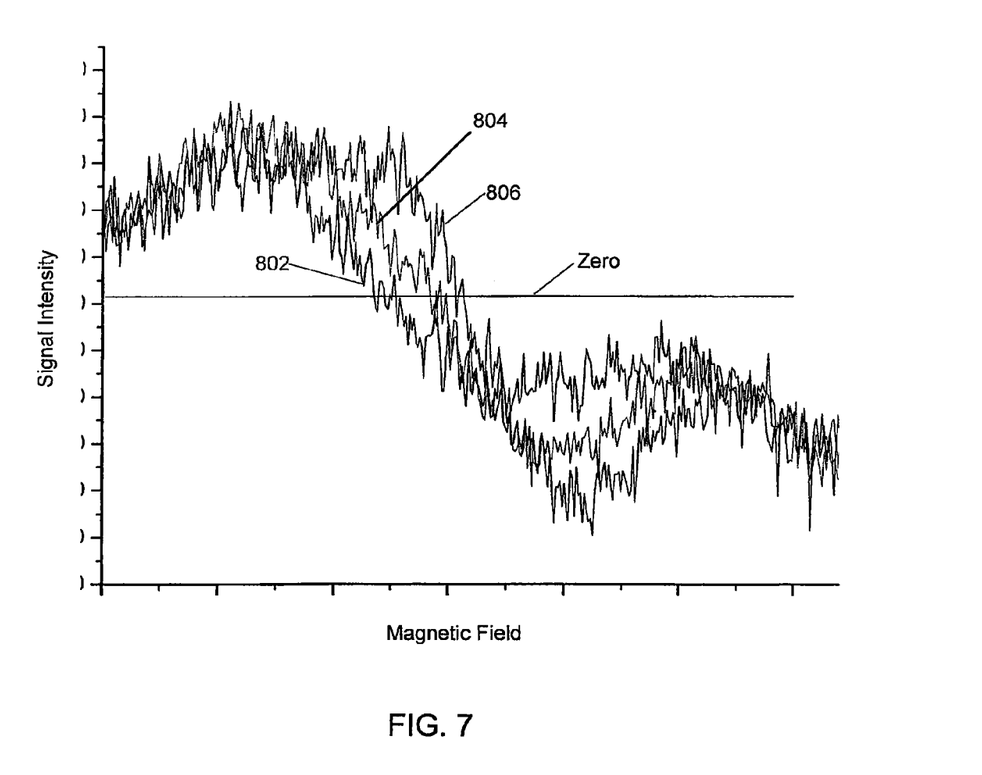
FIG. 7 is an illustration of the shift in frequency of zero-crossover of the resonances with increasing radiation dose.

With reference to FIG. 7, it has also been observed that, in a field or frequency window of a few tenths of a percent near the crossover point of the composite of mechanically and radiation induced signals, the crossover point shifts slightly in the direction of higher field or lower frequency when a strong radiation-induced signal is present, see FIG. 7. FIG. 7 portrays the zero-crossover region spectra of a fingernail sample that has not been irradiated 802, the crossover region spectra of one that has been irradiated at five grays 804, and one that has been irradiated at ten grays 806. All three spectra were taken two minutes after the irradiated or un-irradiated samples were cut into five pieces and placed into a sample holder.

In an alternative embodiment intended for triage purposes in exposed subjects, the RIS is estimated, and triage categories determined, based on the amount of shift in this crossover point and the amount of time and storage temperature since a sample was cut because this shift has been observed to drift with time after cutting. This embodiment determines the shift by using an EPR standard present in the same magnetic field and present in the same spectra as a reference, and determining a difference in frequency or field of the crossover point of the fingernail signal relative to a crossover point of the signal due to the reference.

Figure 9:
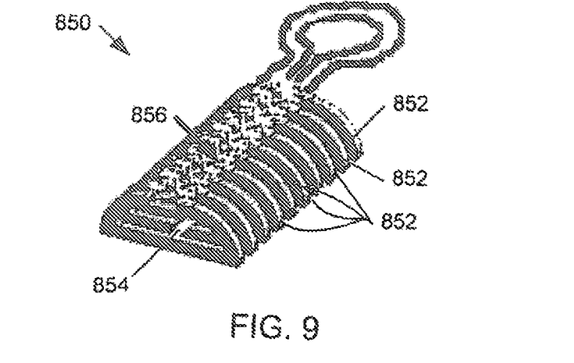
FIG. 9 is a view of an alternative embodiment of a sensing loop device for use in sensing EPR measurements of fingernails as illustrated with reference to FIGS. 2, 3, and 4.

It has been found that resonances in fingernails are more readily detectable and provide a clearer RIS when taken at higher magnetic field strengths and correspondingly higher frequencies. As frequencies are increased, however, non-resonant absorption of radio frequency energy by water in tissues adjacent to intact fingernails becomes an increasingly significant issue. An alternative embodiment for use in measuring radiation dose absorbed by intact fingernails in vivo employs high frequencies, of between 9 and 10 GHz and about 9.5 GHz, with a magnetic field of around 3300 gauss to take advantage of this increased sensitivity. In order to limit penetration of the radio frequency energy into tissues, such as the nailbed, adjacent to or near the fingernail, and attenuation associated with such penetration, this embodiment uses a surface-sensitive resonator 850 (FIG. 9). Other portions of this embodiment resemble those illustrated in FIGS. 2, 3, and 4.

The resonator 850 for use near 9.5 GHz has several closely-spaced D-shaped elements 852 joined by a backbone 854 located in the center of the straight arm or back of the D. Circuitry 856 is provided on a circuit board (not shown in FIG. 9 for clarity, see FIGS. 12 and 13) to reverse polarity in, thereby reversing currents in, adjacent D-shaped elements 852, to produce counter-rotating-currents (CRC) in the D-shaped elements. The CRC causes the electromagnetic fields associated with adjacent D-shaped elements to cancel at distances significantly greater than a spacing of the D-shaped elements 852, while being significant close to the elements.

Because the electromagnetic fields associated with the CRC resonator of FIG. 9 cancel at depths more than a couple of millimeters from the resonator, these fields are most intense and are sensitive to resonances in the fingernail without substantial attenuation by underlying tissues of the finger.

Figure 10:
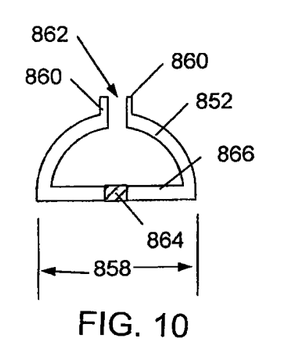
FIG. 10 is a view of one D-shaped element of the sensing loop device of FIG. 9.

An individual D-shaped element 852 is illustrated in FIG. 10. It has a pin 860 on each side of a gap 862 in the curved arm of the D. The backbone 864 in the straight arm 866 of the D is sectioned in the illustration.

In an alternative embodiment resembling that of FIG. 9, the back of each D 852 is slightly concave to more closely fit normal fingernail curvature.

Figure 11:
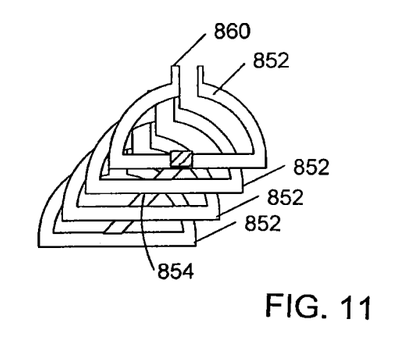
FIG. 11 is a view of several D-shaped elements and their backbone of the device of FIG. 9.

The D-shaped elements 852 are formed by electric discharge machining as a group of from six to ten elements with backbone 854 connecting them as shown in FIG. 11. In an embodiment, the elements 852 are spaced along the backbone with pitch about one millimeter of width 858 of the D about five millimeters The pins 860 of the D-shaped elements 852 are inserted and soldered into plated-through holes 870 (FIG. 12) in a printed-circuit board 872. Circuit board 872, which may be a thin and flexible circuit board, has an etched foil coupling loop 874 that may inductively couple to the pickup coil 668 of electronics 674 in the machine illustrated in FIG. 2. The circuit board has a transmission line portion 876 for transmitting radio frequency energy to the D-shaped elements 852, and which in an alternative embodiment is bent at a 90-degree angle to avoid stray coupling of a 9.5 GHz signal into radiation-absorbent tissues from pickup coil 668 and coupling loop 875. The circuit board also has a pattern of connecting pads and lines 878 that alternate polarity of driving signals at each D-shaped element 852.

Figure 12:
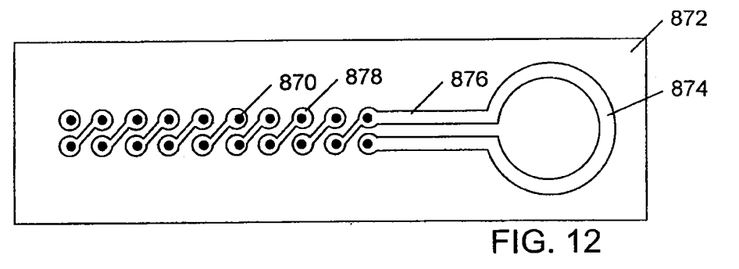
FIG. 12 is a top view of the printed circuit board of the device of FIG. 9.
Figure 13:
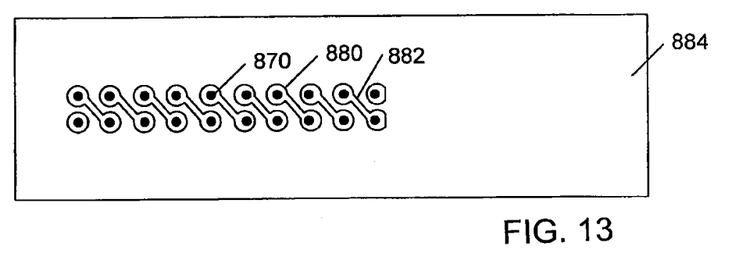
FIG. 13 is a top view of a bottom layer of the printed circuit board of the device of FIG. 9.

In order to complete the alternating polarity of driving signals at each D-shaped element 852, a second or bottom layer 884 of the printed circuit board—shown as a top view so its relationship to the top layer of FIG. 12—is provided as illustrated in FIG. 13. This has the plated through holes 870 also illustrated in FIG. 12, with a pattern of pads 880 and lines 882 that complete the circuit to reverse polarity of driving signals between each D-shaped element 852, thereby providing alternating current direction between each pair of elements 852.

The embodiment of FIG. 2 using the resonator of FIGS. 9-13 is particularly well adapted to triage and diagnostic applications because the resonator can be positioned to avoid the fingernail ends and thereby avoid the mechanically induced signals MIS heretofore discussed; the remaining signal is primarily RIS.

An embodiment of the resonator of FIGS. 9-13 is surface sensitive, in that it is sensitive primarily to material within the range of in contact with the resonator to two millimeters of the resonator. By being sensitive primarily to material within a certain range of distances we mean that, when in contact with a fingernail or other substance exhibiting EPR resonance, eighty percent or better of the resonance signal measured is derived from interactions with substances located within this range of distance from a base of the resonator. An alternative embodiment is primarily sensitive to materials within one and a half millimeters of the resonator.

While the forgoing has been particularly shown and described with reference to particular embodiments thereof, it will be understood by those skilled in the art that various other changes in the form and details may be made without departing from the spirit and scope hereof. It is to be understood that various changes may be made in adapting the description to different embodiments without departing from the broader concepts disclosed herein and comprehended by the claims that follow.

What is claimed is:

1. A microwave resonator for surface EPR comprising:
a resonant electrical coil structure adaptable to be placed in proximity to a surface and having a region of sensitivity substantially limited to a surface thickness; and
a processing circuit for providing a signal to the resonant electrical coil and receiving an EPR signal from the resonant electrical coil to output a measure of chemical properties of the surface;
wherein the resonator consists of a series of substantially parallel loops arrayed along a common axis positionable parallel to the surface in which loops that are adjacent to other loops have opposite polarities of current flow with the loops to which they are adjacent;
wherein the loops are mechanically joined at points of zero electrical potential; and
wherein the loops are electrically joined by a conductor along an axis parallel to an axis of the loops adjacent to the surface.

2. The microwave resonator for surface EPR of claim 1 wherein the resonant electrical coil structure is adaptable to be placed in proximity to an in vivo nail and has a region of sensitivity substantially limited to a single nail thickness; and further including
a processing circuit for providing a signal to the resonant electrical coil and receiving an EPR signal from the resonant electrical coil to output a measure of received radiation dose by the nail.

3. The microwave resonator of claim 2 wherein the loops are D-shaped.

4. The microwave resonator of claim 2 wherein the loops are attached to a printed circuit board providing for crossover traces which alternate electrical current direction between loops that are adjacent to each other.

5. The microwave resonator of claim 2 wherein the nail is selected from the group consisting of an in vivo fingernail and in vivo toenail.

6. The microwave resonator of claim 2 further including a support structure for supporting a human appendage to position the nail adjacent to the coil.

7. The microwave resonator of claim 1 wherein the resonant electrical coil structure is adaptable to be placed in proximity to an in vivo tooth and having a region of sensitivity substantially limited to a depth of the tooth enamel.

8. The microwave resonator of claim 1 further including:
a bench adapted to receive a human hand and stabilize a fingernail in a predetermined scanning position; and
wherein the resonant electrical coil structure is supported with respect to the predetermined scanning position to be proximate to the fingernail and having a region of sensitivity substantially limited to a thickness of the fingernail.

9. The microwave resonator for surface EPR of claim 1 wherein the loops are D-shaped.

10. The microwave resonator for surface EPR of claim 1 wherein the loops are attached to a printed circuit board providing for crossover traces which alternate electrical current direction between loops that are adjacent to each other.

11. The microwave resonator for surface EPR of claim 1 further including a support structure for supporting a human appendage to position a nail adjacent to the coil.

* * * * *